United States Patent
Takahashi et al.

(10) Patent No.: US 9,040,502 B2
(45) Date of Patent: May 26, 2015

(54) ANTI-XDR-TB DRUG, ANTI-MDR-TB DRUG, AND COMBINATION ANTI-TUBERCULOSIS DRUG

(75) Inventors: Yoshiaki Takahashi, Tokyo (JP); Masayuki Igarashi, Tokyo (JP); Masaji Okada, Osaka (JP)

(73) Assignees: Microbial Chemistry Research Foundation, Tokyo (JP); Infectious Disease Research Institute WA (US)

( * ) Notice: Subject to any disclaimer, the term of this patent is extended or adjusted under 35 U.S.C. 154(b) by 1044 days.

(21) Appl. No.: 13/075,356

(22) Filed: Mar. 30, 2011

(65) Prior Publication Data

US 2011/0237530 A1 Sep. 29, 2011

Related U.S. Application Data

(63) Continuation of application No. PCT/JP2009/067267, filed on Oct. 2, 2009.

(30) Foreign Application Priority Data

Oct. 2, 2008 (JP) ................................. 2008-257664

(51) Int. Cl.
C07H 19/067 (2006.01)
A61K 31/4409 (2006.01)
A61K 31/496 (2006.01)
A61K 31/7072 (2006.01)

(52) U.S. Cl.
CPC .......... *C07H 19/067* (2013.01); *A61K 31/4409* (2013.01); *A61K 31/496* (2013.01); *A61K 31/7072* (2013.01)

(58) Field of Classification Search
CPC ............ A61K 31/4409; A61K 31/496; A61K 31/7072; C07H 19/067
See application file for complete search history.

(56) References Cited

U.S. PATENT DOCUMENTS

| | | | |
|---|---|---|---|
| 6,780,616 B1 * | 8/2004 | Takeuchi et al. | 435/74 |
| 7,482,439 B2 * | 1/2009 | Miyake et al. | 536/16.8 |
| 2006/0178319 A1 * | 8/2006 | Miyake et al. | 514/43 |

FOREIGN PATENT DOCUMENTS

| | | |
|---|---|---|
| CA | 2 514 930 | 8/2004 |
| CA | 2660818 | 2/2008 |
| JP | 2007-537242 | 12/2007 |
| WO | 01/12643 | 2/2001 |
| WO | 2004/067544 | 8/2004 |
| WO | 2005/107809 | 11/2005 |

OTHER PUBLICATIONS

"Emergence of XDR-TB" by the World Health Organization (2006). Retrieved [online] at <http://www.who.int/mediacentre/news/notes/2006/np23/en/>.*
Blomberg, B., Spinaci, S., Fourie, B., Laing, R. (2001) The rationale for recommending fixed-dose combination tablets for treatment of tuberculosis. Bulletin of the World Health Organization, vol. 79, p. 61-68.*
Ferwerda, G., Kullberg, B.J., de Jong, D.J., Girardin, S.E., Langenberg, D.M.L., van Crevel, R., Ottenhoff, T.H.M., Van der Meer, J.W.M., Netea, M.G. (2007) *Mycobacterium paratuberculosis* is recognized by Toll-like receptors and NOD2. Journal of Leukocyte Biology, vol. 82, p. 1011-1018.*
Masakazu, Aoki, Fukujuji, 5, 16-17, 2007, XDR-TB (Extensively Drug-Resistant Tuberculosis).
Yuko Kasumi, et al., Kekkaku, vol. 82, No. 12:891-895, 2007.
Chunichi Shimbun, Dec. 5, 2006, Extensively Drug-Resistant Tuberculosis Bacteria Appearing even in Japan.
Nuermberger et al., Combination Chemotherapy with the Nitroimidazopyran PA-824 and First-Line Drugs in a Murine Model of Tuberculosis, Antimicrobial Agents and Chemotherapy, vol. 50, No. 8, pp. 2621-2625 (Aug. 2006).

* cited by examiner

*Primary Examiner* — Scarlett Goon
(74) *Attorney, Agent, or Firm* — Carmody Torrance Sandak & Hennessey LLP

(57) ABSTRACT

A method for treating an individual infected with XDR-TB, the method including administering to the individual an anti-XDR-TB drug which comprises a compound having a structure expressed by Structural Formula (1) below:

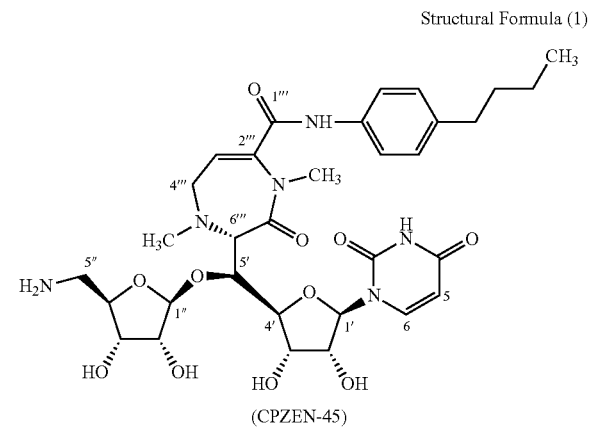

Structural Formula (1)

(CPZEN-45)

3 Claims, 8 Drawing Sheets

ANTI-XDR-TB DRUG, ANTI-MDR-TB DRUG, AND COMBINATION ANTI-TUBERCULOSIS DRUG

CROSS-REFERENCE TO RELATED APPLICATION

This is a continuation application of PCT/JP2009/067267, filed on Oct. 2, 2009.

BACKGROUND OF THE INVENTION

1. Field of the Invention

The present invention relates to an anti-XDR-TB drug effective to extensively drug-resistant tuberculosis (XDR-TB) bacteria, an anti-MDR-TB drug effective to multidrug-resistant tuberculosis (MDR-TB) bacteria, and a combination anti-tuberculosis drug effective to drug-sensitive tuberculosis bacteria.

2. Description of the Related Art

Among infections worldwide, tuberculosis is known to be a disease of which the largest number of people died as a single infection. Tuberculosis bacteria are prone to be resistant due to incorrect treatments such as withdrawal of a drug before curing. For example, multidrug-resistant tuberculosis (MDR-TB) bacteria are known.

The multidrug-resistant tuberculosis bacteria are bacteria resistant to potent first-line drugs of isonicotinic acid hydrazide (INH) and rifampicin (RFP).

In recent years, extensively drug-resistant tuberculosis (XDR-TB) bacteria have been detected from such multidrug-resistant tuberculosis bacteria, which raise serious problems. The extensively drug-resistant tuberculosis bacteria are resistant not only to the first-line drugs but also to second-line drugs of fluoroquinone drugs and, at least, one of amikacin, capreomycin and kanamycin (see, for example, Masakazu, Aoki, Fukujuji, 5, 16-17, 2007; and Yuko Kasumi, et al., Kekkaku, Vol. 82, No. 12: 891-896, 2007). In addition, the extensively drug-resistant tuberculosis bacteria are detected from tuberculosis patients in Japan, and problematically, such patients are forced to be isolated (see, for example, Chunichi Shimbun, Dec. 5, 2006, evening newspaper, first page).

Hitherto, therapeutic drugs having excellent pharmaceutical efficacy against such extensively drug-resistant tuberculosis bacteria have not yet been developed. Thus, at present, keen demand has arisen for development of therapeutic drugs thereagainst.

BRIEF SUMMARY OF THE INVENTION

The present invention aims to solve the above existing problems and achieve the following objects. Specifically, an object of the present invention is to provide an anti-XDR-TB drug having an excellent pharmaceutical efficacy against extensively drug-resistant tuberculosis bacteria, an anti-MDR-TB drug having an excellent pharmaceutical efficacy against multidrug-resistant tuberculosis bacteria, and a combination anti-tuberculosis drug having an excellent pharmaceutical efficacy against tuberculosis bacteria sensitive to existing anti-tuberculosis drugs.

The present inventors conducted extensive studies to solve the above existing problems and have found that among the caprazamycin derivatives disclosed by the present inventors in their previous invention (International Publication No. WO2004/067544), the compound having a structure expressed by the following Structural Formula (1) had an excellent antibacterial activity against extensively drug-resistant tuberculosis bacteria and multidrug-resistant tuberculosis bacteria and that combinational use of the compound having Structural Formula (1) and at least one selected from anti-tuberculosis drugs containing rifampicin and anti-tuberculosis drugs containing isonicotinic acid hydrazide (INH) exhibited an excellent antibacterial activity against tuberculosis bacteria sensitive to existing anti-tuberculosis drugs. On the basis of these findings, the present inventors have completed use inventions of the compound having Structural Formula (1) as an anti-XDR-TB drug, an anti-MDR-TB drug and a combination anti-tuberculosis drug.

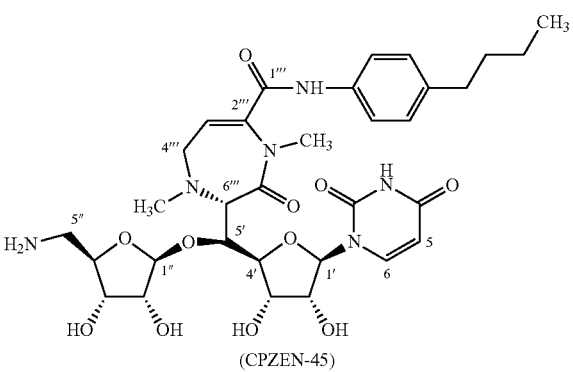

Structural Formula (1)

(CPZEN-45)

The present invention is based on the above findings obtained by the present inventors. Means for solving the above existing problems are as follows.

<1> An anti-XDR-TB drug including:

a compound having a structure expressed by Structural Formula (1) below:

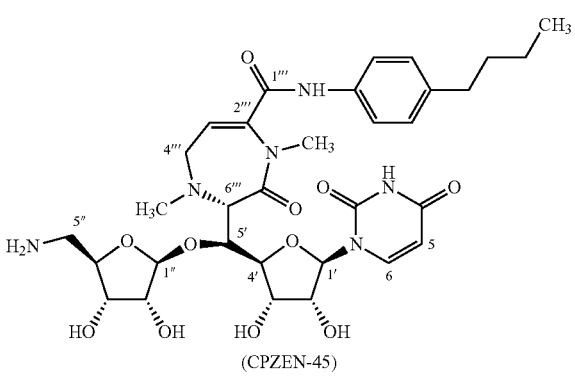

Structural Formula (1)

(CPZEN-45)

<2> An anti-MDR-TB drug including:

a compound having a structure expressed by Structural Formula (1) below:

Structural Formula (1)

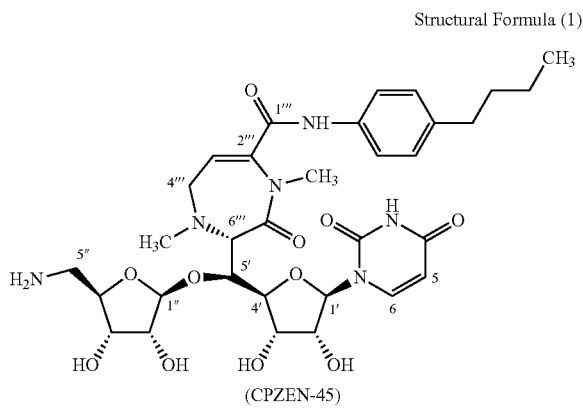 [SMILES: CCCCc1ccc(NC(=O)C2=CCN(C)[C@@H]([C@H](O[C@@H]3O[C@H](CN)[C@@H](O)[C@H]3O)[C@H]3O[C@@H](n4ccc(=O)[nH]c4=O)[C@H](O)[C@@H]3O)C(=O)N2C)cc1]

(CPZEN-45)

<3> A combination anti-tuberculosis drug including:

a drug containing a compound having a structure expressed by Structural Formula (1) below, and at least one anti-tuberculosis drug selected from an anti-tuberculosis drug containing rifampicin (RFP) and an anti-tuberculosis drug containing isonicotinic acid hydrazide (INH).

Structural Formula (1)

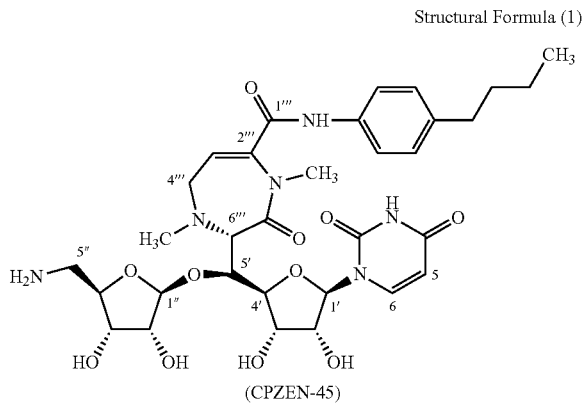 [SMILES: CCCCc1ccc(NC(=O)C2=CCN(C)[C@@H]([C@H](O[C@@H]3O[C@H](CN)[C@@H](O)[C@H]3O)[C@H]3O[C@@H](n4ccc(=O)[nH]c4=O)[C@H](O)[C@@H]3O)C(=O)N2C)cc1]

(CPZEN-45)

<4> A method for treating an individual infected with XDR-TB, the method including:

administering to the individual the anti-XDR-TB drug according to <1>.

<5> A method for treating an individual infected with MDR-TB, the method including:

administering to the individual the anti-MDR-TB drug according to <2>.

<6> A method for treating an individual infected with drug-sensitive tuberculosis bacteria, the method including:

administering to the individual the combination anti-tuberculosis drug according to <3>.

The present invention can provide an anti-XDR-TB drug having an excellent pharmaceutical efficacy against extensively drug-resistant tuberculosis bacteria, an anti-MDR-TB drug having an excellent pharmaceutical efficacy against multidrug-resistant tuberculosis bacteria, and a combination anti-tuberculosis drug having an excellent pharmaceutical efficacy against tuberculosis bacteria sensitive to existing anti-tuberculosis drugs. These can solve the above existing problems and achieve the above objects.

DETAILED DESCRIPTION OF THE INVENTION (Anti-XDR-TB Drug and Anti-MDR-TB Drug)

An anti-XDR-TB drug of the present invention contains at least a compound having the following Structural Formula (1); and, if necessary, further contains other ingredients.

An anti-MDR-TB drug of the present invention contains at least a compound having the following Structural Formula (1); and, if necessary, further contains other ingredients.

Structural Formula (1)

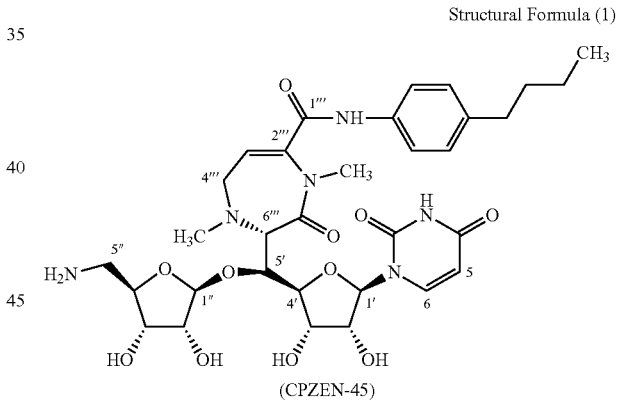

(CPZEN-45)

The XDR-TB (extensively drug-resistant tuberculosis) bacteria are resistant to two main first-line drugs of isonicotinic acid hydrazide (INH) and rifampicin (RFP) and are resistant to second-line drugs of fluoroquinolone drugs and, at least, one of amikacin, capreomycin and kanamycin.

The MDR-TB (multidrug-resistant tuberculosis) bacteria are resistant to two main first-line drugs of isonicotinic acid hydrazide (INH) and rifampicin (RFP).

—Compound Having Structural Formula (1)—

The name of the compound having Structural Formula (1) according to the systematic nomenclature is (S)-2-{[(2S,3R,4S,5R)-(5-aminomethyl-3,4-dihydroxyoxolan-2-yl)oxy][(2S,3S,4R,5R)-5-(2,4-dioxo-1,2,3,4-tetrahydropyrimidin-1-yl)-3,4-dihydroxyoxolan-2-yl]-(S)-methyl}-N-(4-butylphenyl)-1,4-dimethyl-3-oxo-1H-1,4-diazepine-5-carboxamide. Hereinafter, the compound having Structural Formula (1) may be referred to as "CPZEN-45."

—Physico-Chemical Properties—

Figure 1:
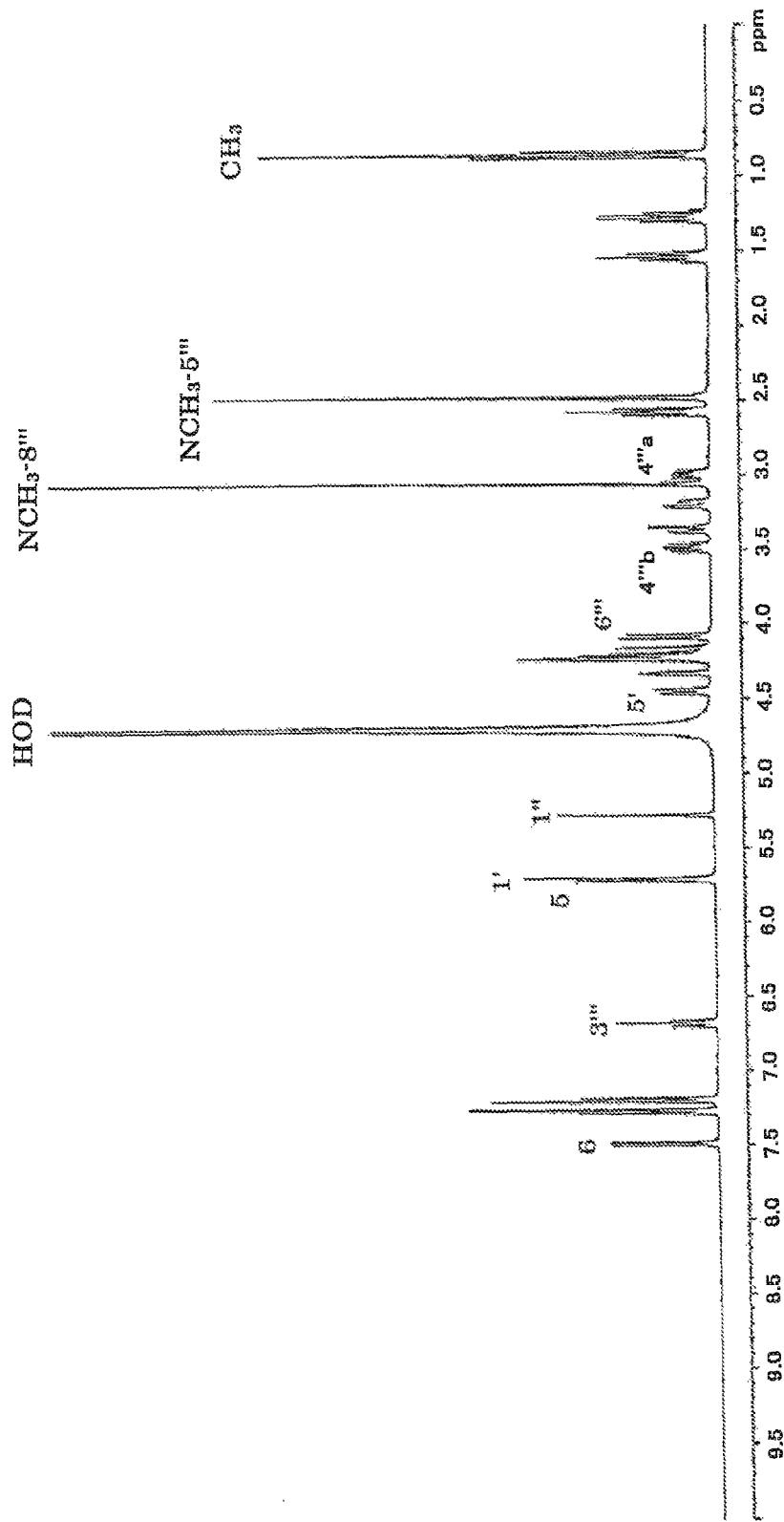
FIG. 1 is a $^1$H-NMR spectrum of CPZEN-45 trifluoroacetate in $D_2O$ at 500 MHz (the unit of the horizontal axis: ppm).
Figure 2:
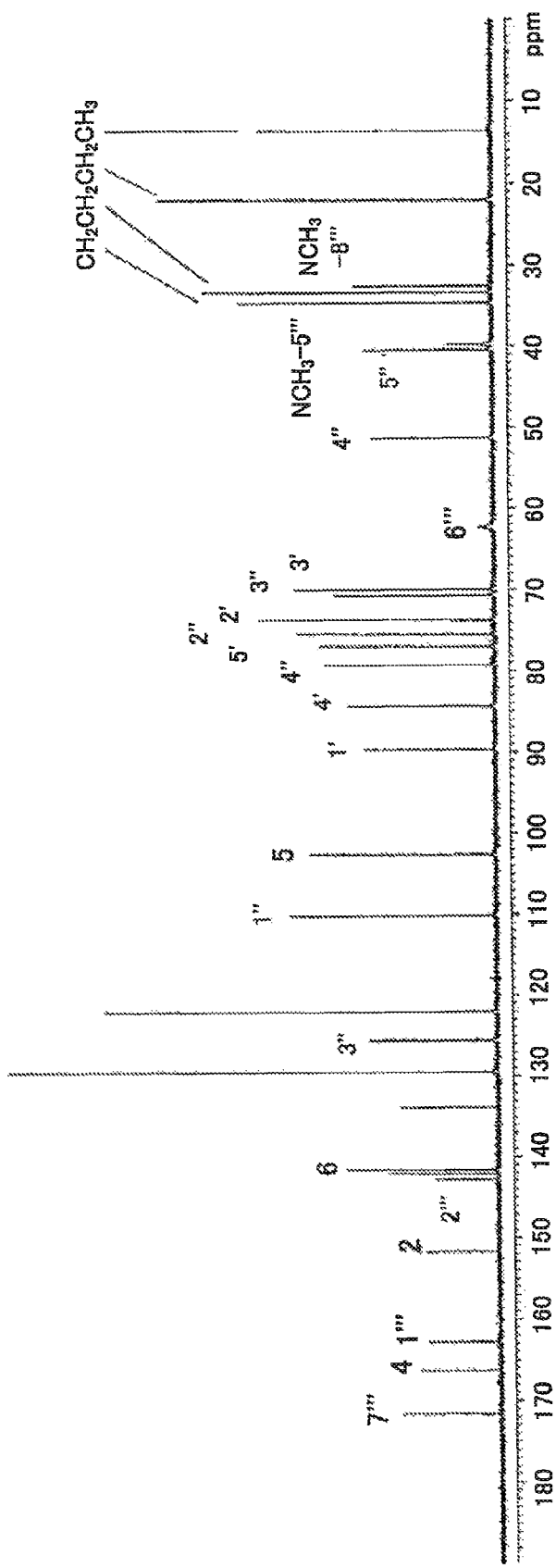
FIG. 2 is a $^{13}$C-NMR spectrum of CPZEN-45 trifluoroacetate in $D_2O$ at 125.8 MHz (the unit of the horizontal axis: ppm).

Physico-chemical properties of the compound having Structural Formula (1) as its trifluoroacetate are as follows.
(1) Melting point: 175° C.-177° C. (decomposition)
(2) Specific rotation: $[\alpha]_D^{22}$ +79° (c1, MeOH)
(3) Mass spectrum (ESI-MS): m/z 801 [M+CF$_3$COOH—H]$^-$
(4) $^{19}$F-NMR spectrum (376.5 MHz, in deuterated DMSO, Freon 11 internal standard): δ-73.86 (s, CF$_3$)
(5) $^1$H-NMR spectrum (500 MHz, in deuterated water, TMS internal standard): refer to the chart of FIG. 1
(6) $^{13}$C-NMR spectrum (125.8 MHz, in deuterated water, TMS internal standard): refer to the chart of FIG. 2

Whether a compound has a structure expressed by Structural Formula (1) can be determined with appropriately selected various analysis methods. This determination can be performed through, for example, mass spectrum analysis, $^1$H-NMR spectrum analysis and $^{13}$C-NMR spectrum, as described above.

The CPZEN-45 may be in the form of salt. The salt is not particularly limited and may be appropriately selected depending on the intended purpose. Examples thereof include carboxylates (e.g., the above trifluoroacetate, acetate, trichloroacetate, hydroxyacetate, lactate, citrate, tartrate, oxalate, benzoate, butyrate, maleate, propionate, fumarate and malate), inorganic acid salts (e.g., hydrohalic acid salts, sulfate, nitrate, phosphate and carbonate), amino acid salts (e.g., alginate, aspartate and glutamate) and sulfonates (e.g., methanesulfonate and p-toluenesulfonate).

—Production Method for CPZEN-45—

The production method for CPZEN-45 is not particularly limited and may be appropriately selected depending on the intended purpose. CPZEN-45 can be produced by, for example, the method described in International Publication No. WO2004/067544.

The production method for a salt of CPZEN-45 is not particularly limited and may be appropriately selected depending on the intended purpose. For example, the salt of CPZEN-45 can be produced by a commonly known method together with pharmacologically acceptable salts such as carboxylates (e.g., the above trifluoroacetate, acetate, trichloroacetate, hydroxyacetate, lactate, citrate, tartrate, oxalate, benzoate, butyrate, maleate, propionate, fumarate and malate), inorganic acid salts (e.g., hydrohalic acid salts, sulfate, nitrate, phosphate and carbonate), amino acid salts (e.g., alginate, aspartate and glutamate) and sulfonates (e.g., methanesulfonate and p-toluenesulfonate).

—Amount of CPZEN-45 Contained—

The amount of CPZEN-45 or a salt thereof contained in the anti-XDR-TB drug or the anti-MDR-TB drug is not particularly limited and may be appropriately selected depending on the intended purpose. Also, the anti-XDR-TB drug or the anti-MDR-TB drug may be CPZEN-45 or a salt thereof itself.

—Other Ingredients—

The other ingredients contained in the anti-MDR-TB drug or the anti-MDR-TB drug are not particularly limited and may be appropriately selected depending on the intended purpose from, for example, pharmacologically acceptable carriers. Examples thereof include ethanol, water and starch.

The amount of the other ingredients contained in the anti-XDR-TB drug or the anti-MDR-TB drug is not particularly limited, so long as the effects of CPZEN-45 or a salt thereof are not impeded, and may be appropriately determined depending on the intended purpose.

—Use—

Notably, the anti-XDR-TB drug or the anti-MDR-TB drug may be used alone or in combination with a drug containing other active ingredients as described below. Also, the anti-XDR-TB drug or the anti-MDR-TB drug may be incorporated before use into a drug containing other active ingredients.

—Dosage Form—

The dosage form of the anti-XDR-TB drug or the anti-MDR-TB drug is not particularly limited and may be appropriately selected depending on the intended purpose. Examples of the dosage form include powder, capsules, tablets and liquids. The anti-XDR-TB drug or the anti-MDR-TB drug can be formed into each of these dosage forms by a routine method.

—Administration—

The administration method of the anti-XDR-TB drug or the anti-MDR-TB drug is not particularly limited and may be appropriately selected depending on, for example, the dosage form of the anti-XDR-TB drug or the anti-MDR-TB drug. The anti-XDR-TB drug or the anti-MDR-TB drug can be administered orally or parenterally.

The dose of the anti-XDR-TB drug or the anti-MDR-TB drug is not particularly limited and may be appropriately determined considering various factors of target individuals such as their age, body weight, constitution, symptoms and concomitant use of a drug containing other active ingredients.

The time of administration of the anti-XDR-TB drug or the anti-MDR-TB drug is not particularly limited and may be appropriately selected depending on the intended purpose.

The animal species to which the anti-XDR-TB drug or the anti-MDR-TB drug is to be administered is not particularly limited and may be appropriately selected depending on the intended purpose. Particularly suitable examples thereof include human.

<Treatment Method>

Since the anti-XDR-TB drug contains the compound having Structural Formula (1), the anti-XDR-TB drug can be administered to an individual infected with XDR-TB to treat the individual infected with XDR-TB. Thus, the present invention relates also to a method for treating an individual infected with XDR-TB including administering the anti-XDR-TB drug to the individual.

Since the anti-MDR-TB drug contains the compound having Structural Formula (1), the anti-MDR-TB drug can be administered to an individual infected with MDR-TB to treat the individual infected with MDR-TB. Thus, the present invention relates also to a method for treating an individual infected with MDR-TB including administering the anti-MDR-TB drug to the individual.

(Combination Anti-Tuberculosis Drug)

A combination anti-tuberculosis drug of the present invention contains a drug containing a compound having Structural Formula (1) (CPZEN-45) and at least one anti-tuberculosis drug selected from existing anti-tuberculosis drugs; and, if necessary, further contains other drugs.

The combination anti-tuberculosis drug of the present invention can be suitably used for tuberculosis bacteria sensitive to existing anti-tuberculosis drugs.

—Drug Containing CPZEN-45—

The drug containing CPZEN-45 is not particularly limited and may be appropriately selected depending on the intended purpose. Examples thereof include the above anti-XDR-TB drug and the above anti-MDR-TB drug.

—Existing Anti-Tuberculosis Drug—

The existing anti-tuberculosis drug is not particularly limited and may be appropriately selected depending on the intended purpose. Examples thereof include those described in the Japanese Pharmacopoeia Fifteenth Edition (Mar. 31, 2006; Announcement No. 285 by the Ministry of Health, Labour and Welfare).

The anti-tuberculosis drug described in the Japanese Pharmacopoeia Fifteenth Edition is not particularly limited and may be appropriately selected depending on the intended purpose. Examples thereof include anti-tuberculosis drugs containing rifampicin (RFP), anti-tuberculosis drugs containing rifampicin derivatives, anti-tuberculosis drugs containing isonicotinic acid hydrazide (INH) and anti-tuberculosis drugs containing isonicotinic acid hydrazide derivatives. Of these, preferred are anti-tuberculosis drugs containing rifampicin (RFP) and anti-tuberculosis drugs containing isonicotinic acid hydrazide (INH).

The rifampicin derivative is not particularly limited and may be appropriately selected depending on the intended purpose. Examples thereof include rifabutin and rifapentine.

The isonicotinic acid hydrazide derivative is not particularly limited and may be appropriately selected depending on the intended purpose. Examples thereof include isonicotinic acid hydrazide.sodium methanesulfonate (IHMS), sodium glucuronate.sonicotinyl hydrazone (INHG) and calcium pyruvate-isoniazone (IP).

—Use—

Notably, the combination anti-tuberculosis drug may be used alone (i.e., only the above drugs are combined) or in combination with a drug containing other active ingredients.

—Dosage Form—

The dosage form of the drug containing CPZEN-45 or the existing anti-tuberculosis drug is not particularly limited and may be appropriately selected depending on the intended purpose. Examples of the dosage form include powder, capsules, tablets and liquids. The drug containing CPZEN-45 or the existing anti-tuberculosis drug can be produced by a routine method.

The combination of the dosage forms of the drug containing CPZEN-45 and the existing anti-tuberculosis drug is not particularly limited and may be appropriately selected depending on the intended purpose. For example, the dosage form of the drug containing CPZEN-45 may be an injection, while the dosage form of the existing anti-tuberculosis drug may be a liquid.

—Administration—

The administration method of the drug containing CPZEN-45 or the existing anti-tuberculosis drug is not particularly limited and may be appropriately selected depending on, for example, the dosage form of the drug containing CPZEN-45 or the existing anti-tuberculosis drug. The drug containing CPZEN-45 or the existing anti-tuberculosis drug can be administered orally or parenterally.

The combination of the administration methods of the drug containing CPZEN-45 and the existing anti-tuberculosis drug is not particularly limited and may be appropriately selected depending on the intended purpose. For example, CPZEN-45 may be parenterally administered, while the existing anti-tuberculosis drug may be orally administered.

The dose of the drug containing CPZEN-45 or the existing anti-tuberculosis drug is not particularly limited and may be appropriately determined considering various factors of target individuals such as their age, body weight, constitution, symptoms and concomitant use of a drug containing other active ingredients.

The combination of the doses of the drug containing CPZEN-45 and the existing anti-tuberculosis drug is not particularly limited and may be appropriately selected depending on the intended purpose. For example, the drug containing CPZEN-45 may be administered at a dose higher than that of the existing anti-tuberculosis drug.

The time of administration of the drug containing CPZEN-45 or the existing anti-tuberculosis drug is not particularly limited and may be appropriately selected depending on the intended purpose.

The combination of the times of administrations of the drug containing CPZEN-45 and the existing anti-tuberculosis drug is not particularly limited and may be appropriately selected depending on the intended purpose. For example, both the drugs may be administered at the same time.

The animal species to which the drug containing CPZEN-45 and the existing anti-tuberculosis drug are administered is not particularly limited and may be appropriately selected depending on the intended purpose. Particularly suitable examples thereof include human.

<Treatment Method>

Since the combination anti-tuberculosis drug contains, in combination, the drug containing the compound having Structural Formula (1) and at least one anti-tuberculosis drug selected from anti-tuberculosis drugs containing rifampicin (RFP) and anti-tuberculosis drugs containing isonicotinic acid hydrazide (INH), the combination anti-tuberculosis drug can be administered to an individual infected with tuberculosis bacteria sensitive to existing anti-tuberculosis drugs (drug-sensitive tuberculosis bacteria) to treat the individual infected with the drug-sensitive tuberculosis bacteria. Thus, the present invention relates also to a method for treating an individual infected with drug-sensitive tuberculosis bacteria including administering the combination anti-tuberculosis drug to the individual.

EXAMPLES

The present invention will next be described in detail by way of Examples and Test Examples, which should not be construed as limiting the present invention thereto. Also, in Examples and Test Examples, the unit "%" means "% by mass" unless otherwise specified.

Example 1

Production of CPZEN-45

Synthesis of Caprazene from Caprazamycin Mixture

Following the below reaction scheme, a mixture (50.0 g) of caprazamycins A to G was dissolved in a solvent mixture (500 mL) of acetic acid-water (4:1). The resultant solution was allowed to react with stirring under heating at 70° C. for 3 hours. The reaction mixture was concentrated, and acetone was added to the obtained concentrated liquid in the form of syrup. The formed precipitates were recovered through filtration, followed by washing with acetone. The obtained brown solid was dissolved in a solvent mixture (1 L) of methanol-water (1:1) and the resultant solution was decolored with active carbon, followed by concentration, to thereby produce 24.3 g of caprazene as a crude solid. This solid was recrystallized from water-acetone (1:2, 750 mL) to produce 17.2 g of caprazene as colorless crystals.

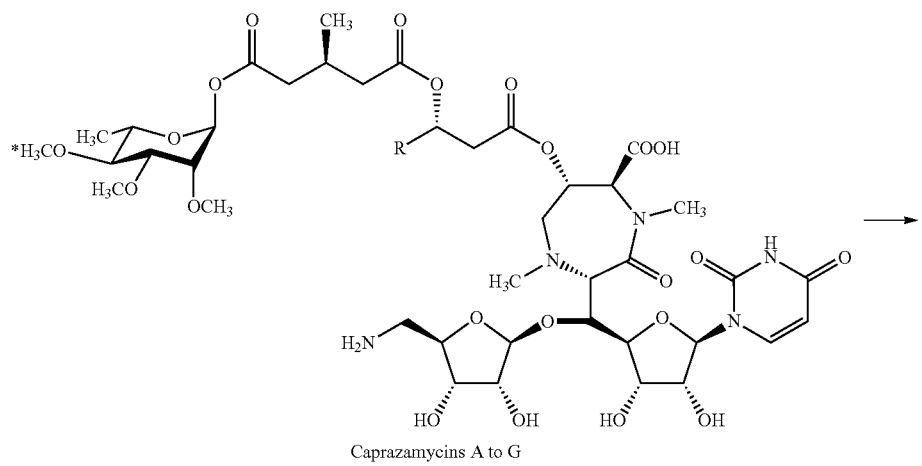

Caprazamycins A to G

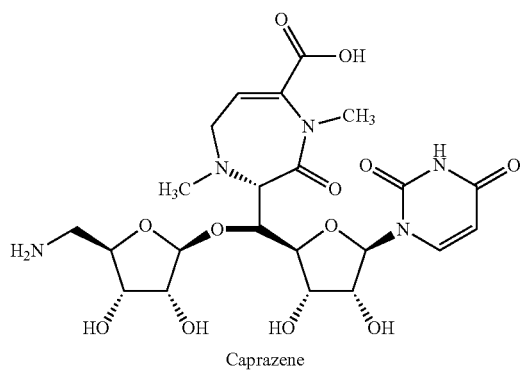

Caprazene

Synthesis of 5″-N-Boc-caprazene from caprazene

Following the below reaction scheme, the above-obtained caprazene crystals (50.0 g) were dissolved in a solvent mixture (600 mL) of water-dioxane (2:1). Then, triethylamine (13.6 g) and di-t-butyl dicarbonate (24.7 g) were added to the resultant solution, followed by stirring at room temperature for 5 hours. Thereafter, concentrated aqueous ammonia (5 mL) was added to the reaction mixture to decompose extra reagents, followed by concentration, to thereby produce 67.2 g of 5″-N-Boc-caprazene (forming a salt together with triethylamine) as a colorless solid.

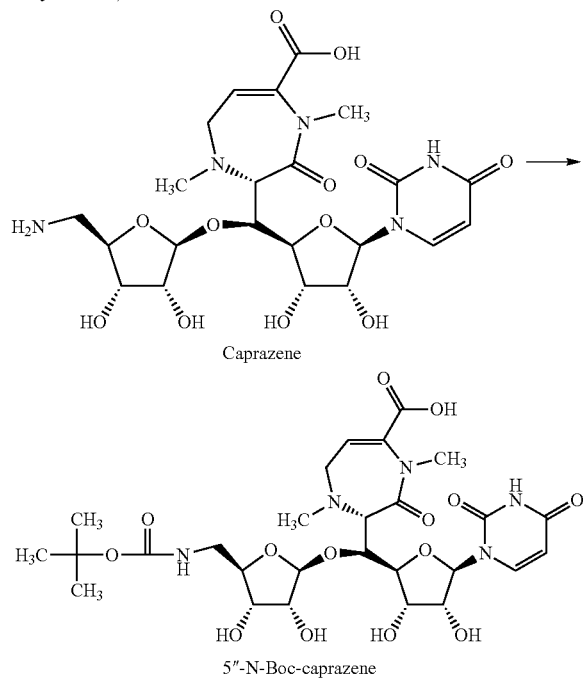

The 5″-N-Boc-caprazene (forming a salt together with triethylamin) was measured for $^1$H-NMR spectrum (500 MHz, in deuterated DMSO, TMS internal standard), which is as follows.

δ1.07 (9H, t, (CH$_3$CH$_2$)$_3$N), 1.36 (9H, s, (CH$_3$)$_3$C—O), 2.32 (3H, s, CH$_3$N-5‴), 2.94 (3H, s, CH$_3$N-8‴), 5.01 (1H, s, H-1″), 5.57 (1H, d, H-1′), 5.59 (1H, d, J=8 Hz, H-5), 6.39 (1H, br t, H-3‴), 7.80 (1H, d, J=8 Hz, H-6)

Synthesis of 5″-N-Boc-caprazene-1‴-amide derivative from 5″-N-Boc-caprazene

Following the below reaction scheme, the above-obtained 5″-N-Boc-caprazene (34.8 g) was dissolved in a mixture (700 mL) of 2-propanol-water (19:1) and 4-butylaniline (7.03 g) and 4-(4,6-dimethoxy-1,3,5-triazin-2-yl)-4-methylmorpholinium chloride hydrate (20.0 g) were added to the resultant solution, followed by reaction with stirring at room temperature for 6 hours.

The reaction mixture was concentrated and the obtained syrup was dissolved in 5% aqueous potassium hydrogensulfate solution (800 mL). The resultant solution was washed with ethyl acetate and then neutralized on ice with 10% aqueous sodium carbonate solution (300 mL). The insoluble matter was extracted with ethyl acetate. The organic layer was washed with saturated brine, dried with anhydrous sodium sulfate and concentrated, to thereby produce 32.2 g of a 5″-N-Boc-caprazene-1‴-amide derivative as a pale yellow solid.

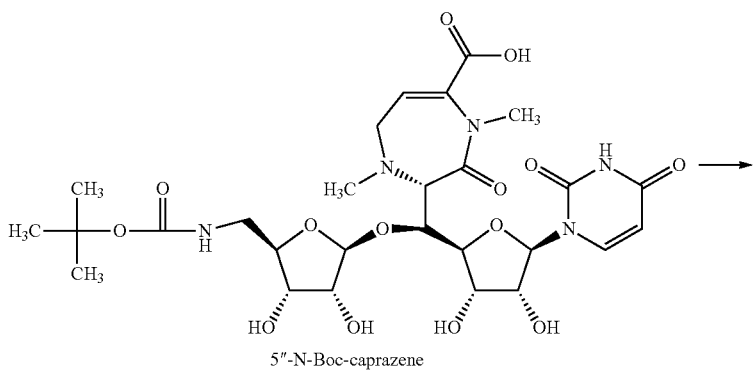

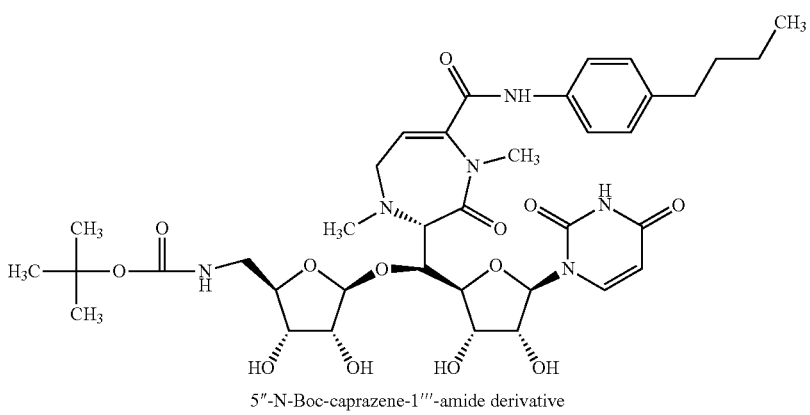

The 5"-N-Boc-caprazene-1'"-amide derivative was measured for $^1$H-NMR spectrum (500 MHz, in deuterated DMSO, TMS internal standard), which is as follows.

δ0.89 (3H, t, C$\underline{H_3}$(CH$_2$)$_3$C$_6$H$_4$NH), 1.31 (9H, s, (CH$_3$)$_3$C—O), 2.35 (3H, s, CH$_3$N-5'"), 2.93 (3H, s, CH$_3$N-8'"), 5.59 (1H, d, J=8 Hz, H-5), 5.63 (1H, s, H-1'), 6.39 (1H, t, H-3'"), 7.13 and 7.51 (each 2H, d, CH$_3$(CH$_2$)$_3$C$_\underline{6}$H$_\underline{4}$NH), 7.79 (1H, d, J=8 Hz, H-6), 10.12 (1H, s, CH$_3$(CH$_2$)$_3$C$_6$H$_4$N$\underline{H}$), 11.30 (1H, s, NH-3)

Synthesis of CPZEN-45 from
5"-N-Boc-caprazene-1'"-amide derivative

Following the below reaction scheme, the above-obtained 5"-N-Boc-caprazene-1'"-amide derivative (23.8 g) was dissolved in a solvent mixture (240 mL) of trifluoroacetic acid-methanol (4:1). The resultant solution was allowed to react at room temperature for 2 hours for removal of the amino-protecting group. The reaction mixture was concentrated and diethyl ether was added to the concentrated syrup. The formed precipitates were washed with diethyl ether and dried, to thereby produce 27.3 g of a pale yellow solid (bis-trifluoroacetate of CPZEN-45).

The obtained solid was dissolved in 1-butanol (1,200 mL) and the resultant solution was washed sequentially with 5% aqueous potassium hydrogensulfate solution and water. The organic layer was decolored with active carbon, followed by concentration, to thereby produce 21.1 g of CPZEN-45 trifluoroacetate as a colorless solid. Next, this solid was crystallized from methanol-hexane, to thereby produce 17.6 g of CPZEN-45 trifluoroacetate as colorless crystals.

The above-produced CPZEN-45 trifluoroacetate crystals were measured for physicochemical properties, which are as follows. From these physico-chemical properties, it was confirmed that CPZEN-45 was a compound having the following Structural Formula (1).

(1) Melting point: 175° C.-177° C. (decomposition)
(2) Specific rotation: [α]$_D^{22}$+79° (c1, MeOH)
(3) Mass spectrum (ESI-MS): m/z 801 [M+CF$_3$COOH—H]$^-$
(4) $^{19}$F-NMR spectrum (376.5 MHz, in deuterated DMSO, Freon 11 internal standard): δ-73.86 (s, CF$_3$)
(5) $^1$H-NMR spectrum (500 MHz, in deuterated water, TMS internal standard): refer to the chart as FIG. 1
(6) $^{13}$C-NMR spectrum (125.8 MHz, in deuterated water, TMS internal standard): refer to the chart as FIG. 2

Structural Formula (1)

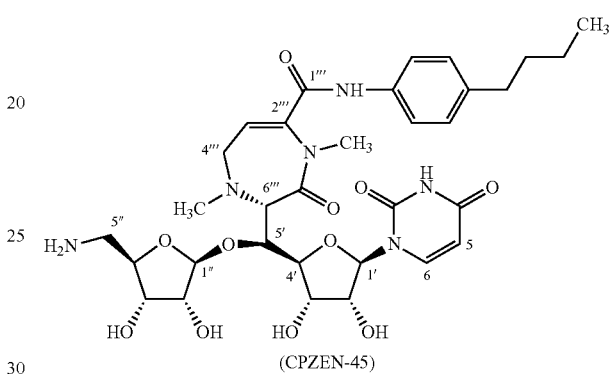

(CPZEN-45)

Also, the obtained CPZEN-45 was used in the following Test Examples 1 to 3.

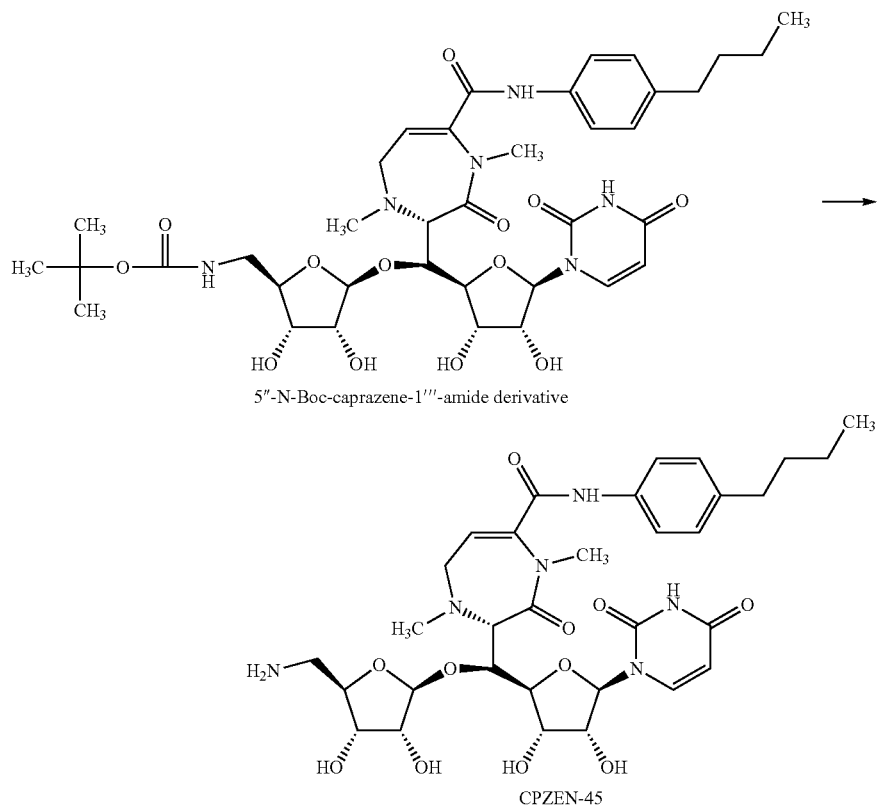

Test Example 1

—Efficacy Evaluation of CPZEN-45 Against Extensively Drug-Resistant Tuberculosis (XDR-TB) Bacteria—

CPZEN-45 was administered to model mice infected with extensively drug-resistant tuberculosis bacteria (XDR-TB) to perform treatment experiments for investigating its efficacy.

—Strains Used—

The extensively drug-resistant tuberculosis (XDR-TB) bacterium for efficacy evaluation of CPZEN-45 was clinical isolate strain *Mycobacterium tuberculosis* XDR-TB (0306-0206), whose drug sensitivity was examined by the ratio method. The results are shown in Table 1. Notably, the sensitivity to pyrazinamide (PZA) was determined on the basis of the presence or absence of pyrazinamidase (PZase) activity. The PZase activity was measured according to the method described in kekkaku Vol. 75, No. 9, pp. 561-562, 2000, by The Japanese Society for Tuberculosis.

TABLE 1

| Drug Name | Test Method | Drug Concentration (µg/mL) | Determination |
|---|---|---|---|
| SM | Ratio Method | 10 | R |
| INH | Ratio Method | 1.0 | R |
| RFP | Ratio Method | 40 | R |
| EB | Ratio Method | 2.5 | R |
| KM | Ratio Method | 20 | R |
| EVM | Ratio Method | 20 | R |
| TH | Ratio Method | 20 | R |
| CS | Ratio Method | 30 | S |
| PAS | Ratio Method | 0.5 | R |
| LVFX | Ratio Method | 1.0 | R |
| PZase | * | * | R |

R: Resistant, S; Sensitive
* According to the method described in kekkaku Vol. 75, No. 9, pp. 561-562, by The Japanese Society for Tuberculosis.

As is clear from Table 1, *M. tuberculosis* XDR-TB (0306-0206) was found to be resistant to streptomycin (SM), isonicotinic acid hydrazide (INH), rifampicin (RFP), ethambutol (EB), kanamycin (KM), ethionamide (TH), enviomycin (EVM), para-amino-salicylic acid (PAS), levofloxacin (LVFX) and pyrazinamide (PZA) while to be sensitive to cycloserine (CS).

—Drug Administration—

Six-week-old female BALB/c mice (forty mice in total) were used for the following Groups 1 to 8 (five mice for each group). $5\times10^5$ colony forming unit (cfu) of *M. tuberculosis* XDR-TB (0306-0206) were intravenously (i.v.) inoculated into each mouse. Drugs were administered to each mouse from the following day of the inoculation. The drugs used were CPZEN-45 and streptomycin (SM, control). These drugs were administered in the following manner. Specifically, each drug was dissolved in physiological saline, and the solution was subcutaneously injected to four parts of the back of each mouse (i.e., left-upper back, right-upper back, left-lower back and right-lower back) at 0.125 mL for each part (total amount: 0.5 mL). The following are the type of a drug administered in each group and its dose.

Group 1: Drug . . . none, Dose . . . none (control)
Group 2: Drug . . . CPZEN-45, Dose . . . 6.3 mg/kg
Group 3: Drug . . . CPZEN-45, Dose . . . 25 mg/kg
Group 4: Drug . . . CPZEN-45, Dose . . . 100 mg/kg
Group 5: Drug . . . CPZEN-45, Dose . . . 200 mg/kg
Group 6: Drug . . . SM, Dose . . . 25 mg/kg
Group 7: Drug . . . SM, Dose . . . 100 mg/kg
Group 8: Drug . . . SM, Dose . . . 200 mg/kg The total number of doses of each drug was 14 times consisting of 5 times (Monday to Friday) at the 1st week, 5 times (Monday to Friday) at the 2nd week, 2 times (Monday and Thursday) at the 3rd week and 2 times (Monday and Thursday) at the 4th week.

—Measurement of Number of Tuberculosis Bacteria (CFU)—

The mice were sacrificed at Day 30 from the administration of the drug. Their lungs, liver and spleen were homogenized and appropriately diluted. The thus-treated samples were each spread on a middlebrook 7H11 agar medium and cultured at 37° C. Thereafter, colonies formed 14 days after were counted to thereby investigate an efficacy in vivo of the drug against the extensively drug-resistant tuberculosis bacteria. The results are shown in FIGS. 3 to 5.

Figure 3:
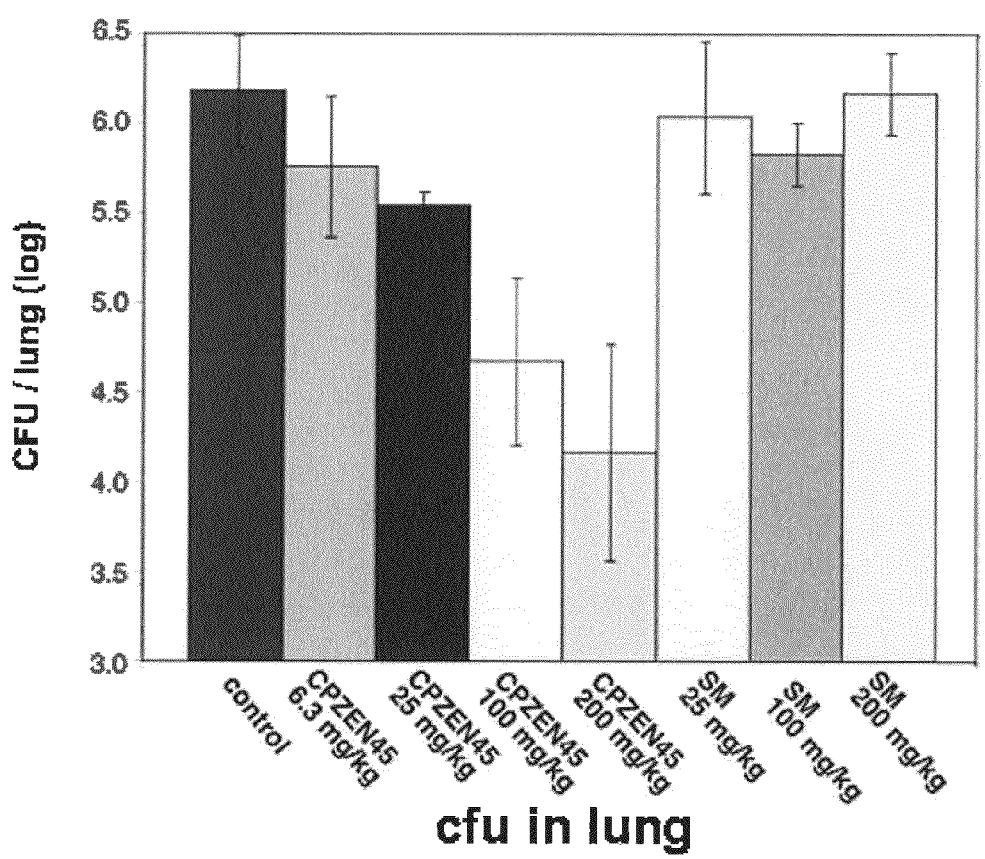
FIG. 3 is a graph indicating the number of tuberculosis bacteria in the lungs in Test Example 1.

FIG. 3 is a graph indicating the number of tuberculosis bacteria in the lungs, where the vertical axis corresponds to the number of bacteria (cfu/g (log)) per mass of the lungs and the bars correspond to Groups 1 to 8 in order from the left. FIG. 4 is a graph indicating the number of tuberculosis bacteria in the liver, where the vertical axis corresponds to the number of bacteria (cfu/g (log)) per mass of the liver and the bars correspond to Groups 1 to 8 in order from the left. FIG. 5 is a graph indicating the number of tuberculosis bacteria in the spleen, where the vertical axis corresponds to the number of bacteria (cfu/g (log)) per mass of the spleen and the bars correspond to Groups 1 to 8 in order from the left.

Figure 4:
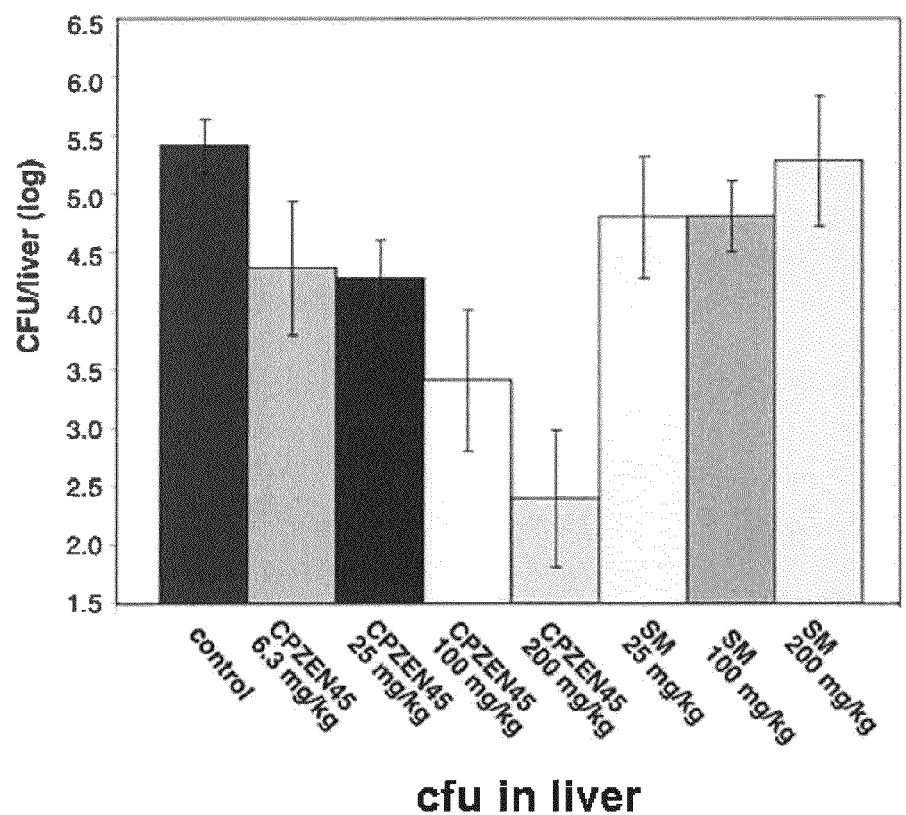
FIG. 4 is a graph indicating the number of tuberculosis bacteria in the liver in Test Example 1.
Figure 5:
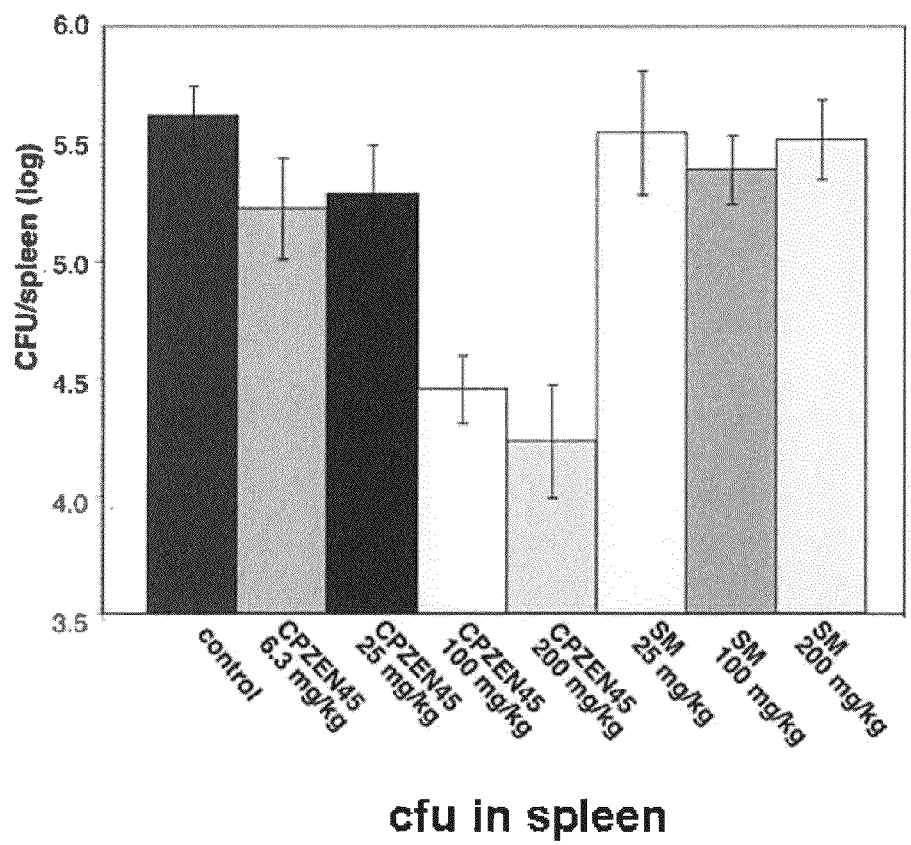
FIG. 5 is a graph indicating the number of tuberculosis bacteria in the spleen in Test Example 1.

As is clear from FIGS. 3 to 5, SM was found to exhibit no antibacterial effects (decrease of the extensively drug-resistant tuberculosis bacteria), while CPZEN-45 was found to exhibit antibacterial effects significantly higher than those of SM against the extensively drug-resistant tuberculosis bacteria with increasing the concentration thereof.

Test Example 2

Antibacterial Spectrum of CPZEN-45 Against Multidrug-Resistant Tuberculosis (MDR-TB) Bacteria and Extensively Drug-Resistant Tuberculosis (XDR-TB) Bacteria Antibacterial spectra of CPZEN-45 against various multidrug-resistant tuberculosis bacteria and extensively drug-resistant tuberculosis (XDR-TB) bacteria resistant to drugs (streptomycin (SM), isonicotinic acid hydrazide (INH), rifampicin (RFP), ethambutol (EB), kanamycin (KM), ethionamide (TH), enviomycin (EVM), para-amino-salicylic acid (PAS), levofloxacin (LVFX), etc.) were obtained according to the standard method of the Japanese Society of Chemotherapy including culturing on a 10% OADC middlebrook 7H10 agar medium at 37° C. and measuring by the multiple dilution method 14 days after. The minimum inhibitory concentration (MIC) for each bacterium is shown in Table 2.

TABLE 2

| organism[1] | medium | MIC (µg/ml)[5] CPZEN-45 | RFP |
|---|---|---|---|
| *M. tuberculosis* MDR (RFP, INH)[1] | 7H10 | 6.25 | >40 |
| *M. tuberculosis* MDR (RFP, INH, KM EB, TH, PAS, EVM)[1] | 7H10 | 6.25 | >40 |
| *M. tuberculosis* MDR (RFP, INH, KM, SM EB, TH)[1] | 7H10 | 6.25 | >40 |

TABLE 2-continued

| organism[1] | medium | MIC (µg/ml)[5] | |
| --- | --- | --- | --- |
| | | CPZEN-45 | RFP |
| M. tuberculosis XDR (RFP, INH, KM EB, TH, PAS, EVM, LVFX)[1] | 7H10 | 6.25 | >40 |

[1]RFP; rifampicin resistant, INH; isoniazid resistant, LVFX; levofloxacin resistant, EB; ethambutol resistant, PAS: para-amino-salicylic acid, TH; ethionamide resistant, KM [1]; kanamycin resistant, SM [1]; streptomycin resistant.

As is clear from Table 2, CPZEN-45 was found to exhibit antibacterial effects against various multidrug-resistant tuberculosis bacteria.

Test Example 3

Combinational Effect of CPZEN-45 and Existing Anti-Tuberculosis Drug on Drug-Sensitive Tuberculosis Bacteria CPZEN-45 and an existing anti-tuberculosis drug were administered in combination to model mice infected with *M. tuberculosis* H37Rv to perform treatment experiments for investigating their efficacy.

—Strain Used—

The drug-sensitive tuberculosis bacterium for combinational efficacy-test of CPZEN-45 was *M. tuberculosis* H37Rv.

—Drug Administration—

Six-week-old female BALB/c mice (fifty mice in total) were used for the following Groups 1 to 10 (five mice for each group). The H37Rv human tuberculosis bacteria ($5 \times 10^5$ cfu) were intravenously (i.v.) inoculated into each mouse. Drugs were administered to each mouse from the following day of the inoculation. The drugs used were CPZEN-45, rifampicin (RFP) and isonicotinic acid hydrazide (INH). Among these drugs, CPZEN-45 was dissolved in physiological saline, and the solution was subcutaneously injected to four parts of the back of each mouse (i.e., left-upper back, right-upper back, left-lower back and right-lower back) at 0.125 mL for each part (total amount: 0.5 mL). RFP or INH was dissolved in 5% gum arabic (which had been dissolved in distilled water) and the solution was injected with a 0.2 mL-oral sonde from the oral esophagus. The following are the type of a drug administered in each group and its dose.

Group 1 (Control):
Drug . . . none, Dose . . . none
Group 2 (RFP):
Drug . . . RFP, Dose . . . 5.0 mg/kg
Group 3 (INH):
Drug . . . INH, Dose . . . 1.5 mg/kg
Group 4 (CPZEN-45 High):
Drug . . . CPZEN-45, Dose . . . 25 mg/kg
Group 5 (RFP+INH):
Drug . . . RFP, INH
Dose . . . RFP 5.0 mg/kg, INH 1.5 mg/kg
Group 6 (CPZEN-45 High+RFP):
Drug . . . CPZEN-45, RFP
Dose . . . CPZEN-45 25 mg/kg, RFP 5.0 mg/kg
Group 7 (CPZEN-45 High+INH):
Drug . . . CPZEN-45, INH
Dose . . . CPZEN-45 25 mg/kg, INH 1.5 mg/kg
Group 8 (CPZEN-45 High+RFP+INH):
Drug . . . CPZEN-45, RFP, INH
Dose . . . CPZEN-45 25 mg/kg, RFP 5.0 mg/kg, INH 1.5 mg/kg
Group 9 (CPZEN-45 Low+RFP+INH):
Drug . . . CPZEN-45, RFP, INH
Dose . . . CPZEN-45 6.3 mg/kg, RFP 5.0 mg/kg, INH 1.5 mg/kg
Group 10 (CPZEN-45 Low):
Drug . . . CPZEN-45, Dose . . . 6.3 mg/kg The total number of doses of each drug was 14 times consisting of 5 times (Monday to Friday) at the 1st week, 5 times (Monday to Friday) at the 2nd week, 2 times (Monday and Thursday) at the 3rd week and 2 times (Monday and Thursday) at the 4th week.

—Measurement of Number of Tuberculosis Bacteria (CFU)—

Figure 7:
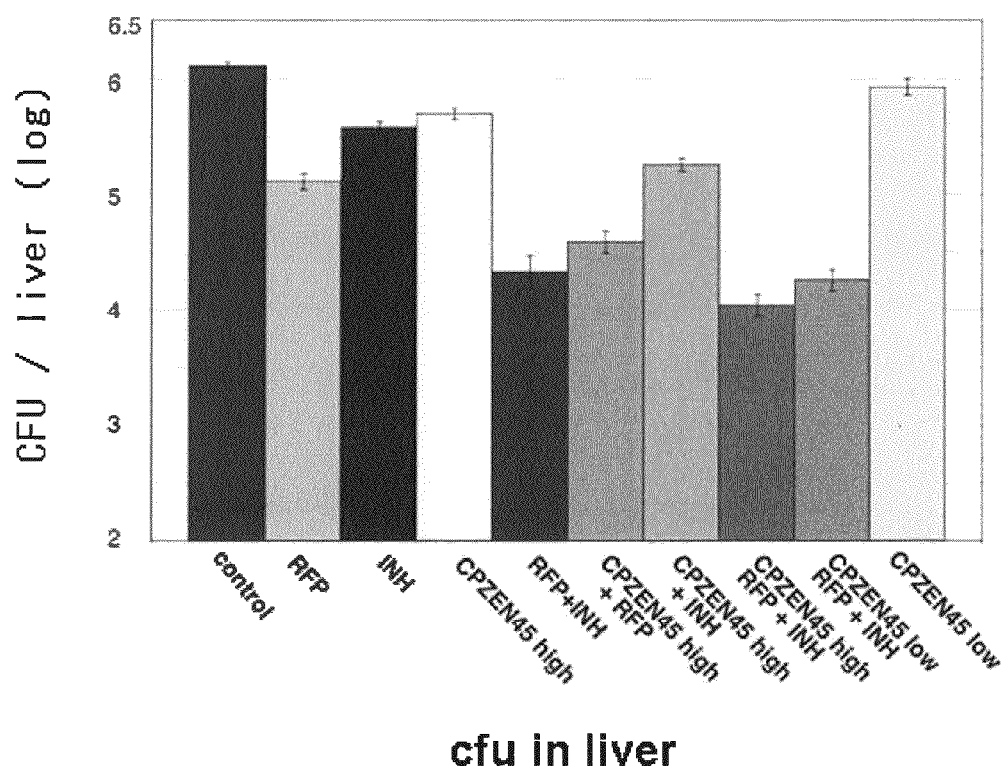
FIG. 7 is a graph indicating the number of tuberculosis bacteria in the liver in Test Example 3.
Figure 8:
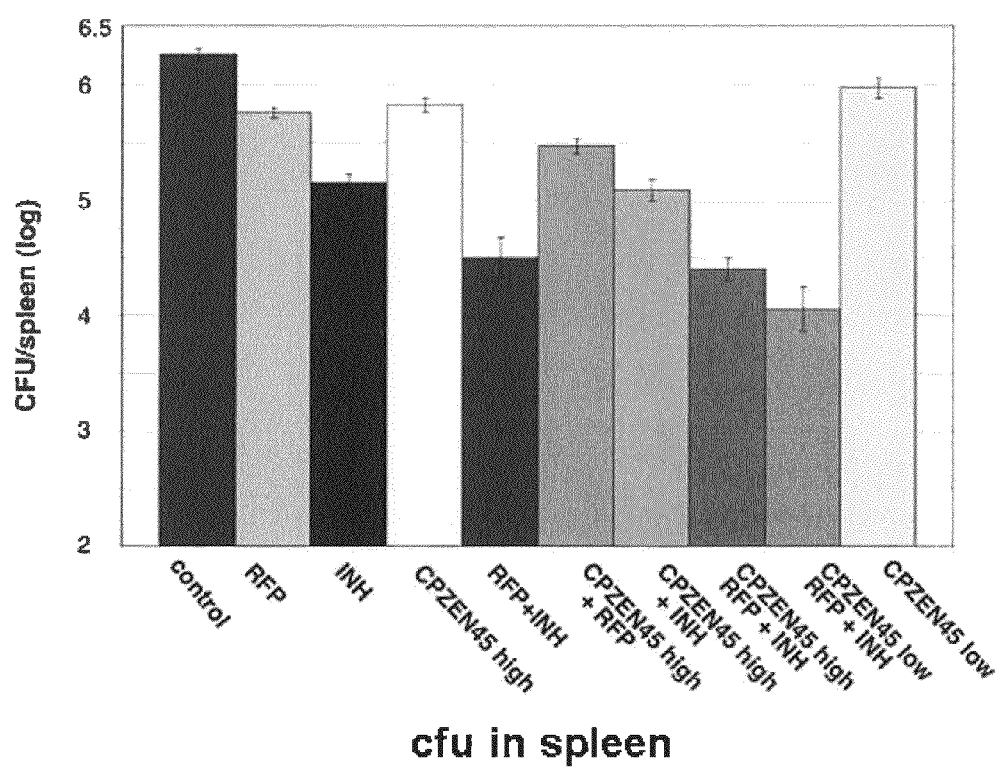
FIG. 8 is a graph indicating the number of tuberculosis bacteria in the spleen in Test Example 3.

The mice were sacrificed at Day 30 from the administration of the drug. Their lungs, liver and spleen were homogenized and seeded on a middlebrook 7H11 agar medium, followed by culturing at 37° C. Thereafter, colonies formed 14 days after were counted to thereby investigate an efficacy in vivo of the combination drug against the drug-sensitive tuberculosis bacteria. The results are shown in FIGS. 6 to 8.

Figure 6:
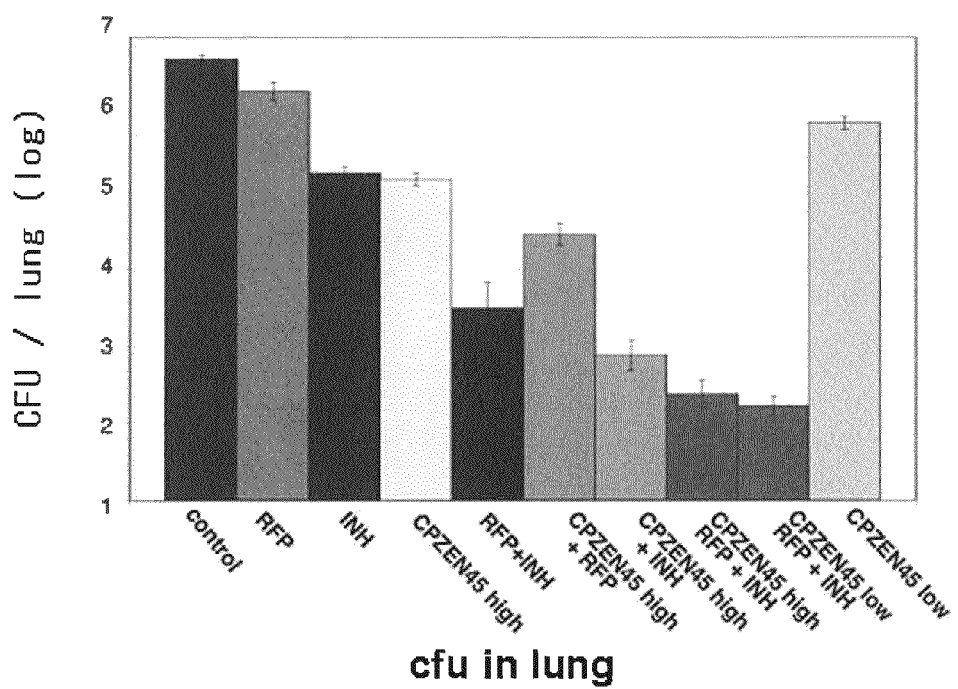
FIG. 6 is a graph indicating the number of tuberculosis bacteria in the lungs in Test Example 3

FIG. 6 is a graph indicating the number of tuberculosis bacteria in the lungs, where the vertical axis corresponds to the number of bacteria (cfu/g (log)) per mass of the lungs and the bars correspond to Groups 1 to 10 in order from the left. From FIG. 6, the number of tuberculosis bacteria in Group 8 (CPZEN-45 high+RFP+INH) was found to be significantly smaller than that in Group 5 (RFP+INH) by the student' t test and the Turkey Kramer test, indicating that the combinational use of CPZEN-45 exhibited synergistic effects. Also, the number of tuberculosis bacteria in Group 9 (CPZEN-45 low+RFP+INH) was found to be significantly smaller than that in Group 5 (RFP+INH).

Furthermore, the number of tuberculosis bacteria in Group 8 (CPZEN-45 high+RFP+INH) was found to significantly smaller than Group 4 (CPZEN-45 high) in which CPZEN-45 was used alone at high concentration. Also, the number of tuberculosis bacteria in Group 9 (CPZEN-45 low+RFP+INH) was found to be significantly smaller than that in Group 10 (CPZEN-45 low) in which CPZEN-45 was used alone at low concentration.

Moreover, the number of tuberculosis bacteria in Group 7 (CPZEN-45 high+INH) was found to be significantly smaller than that in Group 3 (INH) or Group 4 (CPZEN-45 high), indicating that the combinational use of CPZEN-45 exhibited synergistic effects.

Also, the number of tuberculosis bacteria in Group 6 (CPZEN-45 high+RFP) was found to be significantly smaller than that in Group 2 (RFP) or Group 4 (CPZEN-45 high).

From the above results, additional administration of CPZEN-45 with INH and RFP exhibited synergistic effects in the lungs. This result is thought to be important in clinical applications in the future.

FIG. 7 is a graph indicating the number of tuberculosis bacteria in the liver, where the vertical axis corresponds to the number of bacteria (cfu/g (log)) per mass of the liver and the bars correspond to Groups 1 to 10 in order from the left. From FIG. 7, the number of tuberculosis bacteria in Group 8 (CPZEN-45 high+RFP+INH) was found to be significantly smaller than that in Group 5 (RFP+INH). Also, the number of tuberculosis bacteria in Group 8 (CPZEN-45 high+RFP+INH) was found to be significantly smaller than that in Group 4 (CPZEN-45 high) in which CPZEN-45 was used alone at high concentration.

Also, the number of tuberculosis bacteria in Group 7 (CPZEN-45 high+INH) was found to be significantly smaller than that in Group 3 (INH) or Group 4 (CPZEN-45 high).

Also, the number of tuberculosis bacteria in Group 6 (CPZEN-45 high+RFP) was found to be synergistically smaller than that in Group 2 (RFP) or Group 4 (CPZEN-45 high).

From the above results, synergistic effect of CPZEN-45 and RFP could be observed in the liver. Also, additional administration of CPZEN-45 (25 mg/kg) with INH and RFP was found to further decrease the number of tuberculosis bacteria.

FIG. 8 is a graph indicating the number of tuberculosis bacteria in the spleen, where the vertical axis corresponds to the number of bacteria (cfu/g (log)) per mass of the spleen and the bars correspond to Groups 1 to 10 in order from the left. From FIG. 8, the number of tuberculosis bacteria in Group 9 (CPZEN-45 low+RFP+INH) was found to be significantly smaller than that in Group 5 (RFP+INH). Also, the number of tuberculosis bacteria in Group 7 (CPZEN-45 high+INH) was found to be significantly smaller than that in Group 3 (INH) or Group 4 (CPZEN-45 high).

From the above results, in the spleen, additional administration of a low concentration of CPZEN-45 (6.3 mg/kg) with INH and RFP was found to significantly exhibit synergistic effects.

From the above results, it was found that additional administration of not only high-concentration CPZEN-45 (25 mg/kg) but also low-concentration CPZEN-45 (6.3 mg/kg) in combination with INH and RFP can be expected to exhibit synergistic effects of decreasing the number of tuberculosis bacteria.

INDUSTRIAL APPLICABILITY

The anti-MDR-TB drug of the present invention has excellent antibacterial activity against extensively drug-resistant tuberculosis bacteria, and thus can be suitably used for treating patients infected with extensively drug-resistant tuberculosis bacteria which raise serious problems at present.

The anti-MDR-TB drug of the present invention has excellent antibacterial activity against multidrug-resistant tuberculosis bacteria, and thus can be suitably used for treating patients infected with multidrug-resistant tuberculosis bacteria.

The combination anti-tuberculosis drug of the present invention has excellent antibacterial activity against drug-sensitive tuberculosis bacteria, and thus can be expected to shorten a required treatment period as compared with in existing drugs.

What is claimed is:

1. A method for treating an individual infected with extensively drug-resistant tuberculosis, the method comprising:
administering to the individual an anti-extensively drug-resistant tuberculosis drug which comprises a compound having a structure expressed by Structural Formula (1) below:

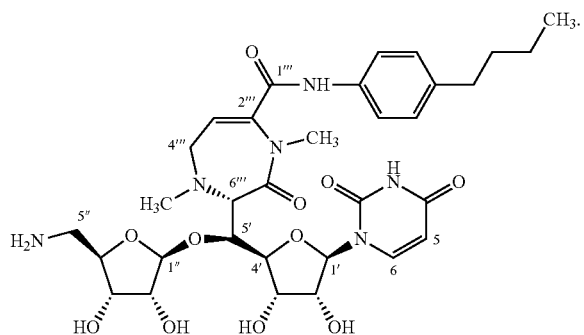

Structural Formula (1)

2. A method for treating an individual infected with multidrug-resistant tuberculosis, the method comprising:
administering to the individual an anti-multidrug-resistant tuberculosis drug which comprises a compound having a structure expressed by Structural Formula (1) below:

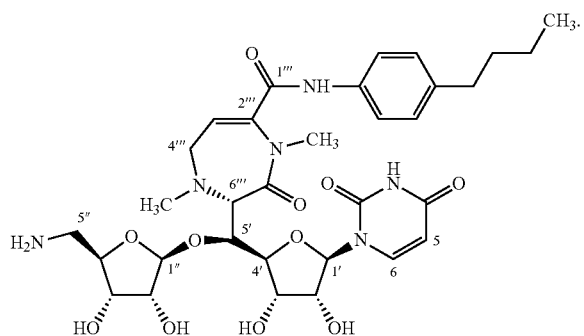

Structural Formula (1)

3. A method for treating an individual infected with drug-sensitive tuberculosis bacteria, the method comprising:
administering to the individual a drug, wherein the drug comprises (i) compound having a structure expressed by Structural Formula (1) below:

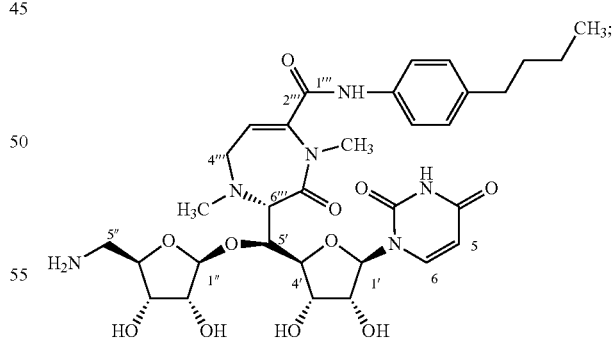

Structural Formula (1)

and (ii) at least one anti-tuberculosis drug selected from rifampicin (RFP) and isonicotinic acid hydrazide (INH).

* * * * *